United States Patent [19]

Kurz

[11] 4,244,688

[45] * Jan. 13, 1981

[54] PULSATING ORTHODONTIC APPLIANCE

[76] Inventor: Craven H. Kurz, 10921 Wilshire Blvd. Suite 512, Los Angeles, Calif. 90024

[*] Notice: The portion of the term of this patent subsequent to Jul. 11, 1995, has been disclaimed.

[21] Appl. No.: 36,040

[22] Filed: May 4, 1979

Related U.S. Application Data

[63] Continuation-in-part of Ser. No. 895,438, Apr. 11, 1978, which is a continuation-in-part of Ser. No. 717,090, Aug. 24, 1976, abandoned.

[51] Int. Cl.$^3$ .......................... A61C 7/00; A61H 1/00
[52] U.S. Cl. ...................................... 433/5; 128/24 A
[58] Field of Search ........................... 433/5; 128/24 A

[56] References Cited

U.S. PATENT DOCUMENTS

| | | | |
|---|---|---|---|
| 3,909,945 | 10/1975 | Foxman | 433/5 |
| 4,123,844 | 11/1978 | Kurz | 433/5 |

Primary Examiner—Gene Mancene
Assistant Examiner—Michael J. Foycik, Jr.
Attorney, Agent, or Firm—Keith D. Beecher

[57] ABSTRACT

An orthodontic appliance is provided which applies a pulsating force to the tooth to be moved, rather than a continuous force as in the case with the prior art devices. The invention is predicated on the concept that when pulsating forces are applied to the tooth, there is little or no hyalinization and consequently more cellular activity, giving rise to more oesteoclastic activity for bone resorption and more oesteoblastic activity for bone opposition. Moreover, the pulsational effect of the tooth on the adjacent periodontal membrane and bone tends to loosen their fibrous structure, and helps the tooth to find a path of least resistance through the bone.

4 Claims, 5 Drawing Figures

PULSATING ORTHODONTIC APPLIANCE

This application is a continuation-in-part of Copending Application Ser. No. 895,438 filed Apr. 11, 1978 which, in turn is a continuation-in-part of Application Ser. No. 717,090 filed Aug. 24, 1976, now abandoned.

BACKGROUND OF THE INVENTION

The conventional method of orthodontic tooth movement, as practiced in the prior art, has been one of constant pressure applied to the tooth in order to move the tooth through the adjacent bone. Constant pressure applied to the periodontal membrane by traditional orthodontic appliances causes the periodontal fibers to become cell-free which results in stand-still of the tooth. Compression of tissue results in reduced blood supply and tissue necrosis, and the tooth will not move again until the bone subjacent to the hyalinized tissue has been eliminated by undermining resorption. Generally, it is essentially the magnitude of the force which will determine the duration of the hyalinization. Moreover, strong forces produce a wide hyalinization area of long duration. A discussion of this phenomena may be found on Pages 76 and 97 of Current Orthodontic Concepts and Techniques, T. M. Graber, Editor, published by W. B. Saunders & Co., 1969.

When a tooth is tipped by a continuous force exerted on it by a usual prior art orthodontic appliance, the peridontal membrane is compressed in a circumscribed area situated close to the alveolar crest. This area becomes cell-free and the blood vessels are occluded, and oesteoclastic activity is reduced to a minimum. A description of this occurrence may be found, for example, at Page 497 of Orthodontic Principles and Practice by Graber, Second Edition, published by Saunders & Co., 1967. If the pressure area of the periodontal membrane during the movement of a tooth by an orthodontic device is not compressed by strong forces, then the formation of oesteoclasts, the cells responsible for resorption of bone, will be enhanced. The flow of blood to the area will not be restricted, and consequently oesteoclastic activity will be more vigorous and bone resorption will be increased.

As stated above, the orthodontic appliance of the present invention introduces pressure impulses to the tooth being moved, rather than a continuous force. With every pressure impulse from the appliance of the invention, the tissue pressure in the periodontal membrane and adjacent bone tissue will be increased. When the pressure is relaxed, the tissue pressure in the peridontal membrane and adjacent bone tissue will be reduced. This fluctuation from high pressure to low pressure in the periodontal and adjacent tissue will result in a pump-like action that will suck blood and tissue fluid into the area, and will then expel fluid from the area, for each cycle of operation. This serves to increase the cellular action around the moving tooth, giving rise to more oesteoclasts for bone resorption and more oesteoblasts for bone apposition.

The active exchange of fluid during the pulsating operation of the appliance of the invention helps carry the by-products of bone resorption out of the resorption area. The pulsating tooth movement produced by the appliance of the invention is physiological and dynamic in nature, rather than pathological. Because the pulsation pressure exerted by the appliance of the invention does not result in areas of hyalinization and necrosis, there is no root resorption or horizontal bone loss during the operation. The pump-like action of the tooth being pulsated by the appliance of the invention is the same on the tension side of the tooth as on the compression side, but opposite in the timing cycle. On the tension side of the tooth, the increased blood supply results in increased cellular activity. The bone building cell is the oesteoblast. The oesteoblastic activity acts in a maximal manner during pulsating tooth movement, resulting in increased bone formation and active stabilization.

To reiterate, pulsation pressure optimal in magnitude and frequency, as produced by the appliance of the invention, is the ideal force for tooth movement because blood supply to the adjacent tissue is not reduced, but due to cyclic positive and negative tissue fluid pressures, a pump-like action is set up in the tissue creating greater blood supply. This enhanced blood supply results in increased oesteoclastic cellular action for the resorption of bone and increased oesteoblastic cellular action for the deposition of new bone elements. Greater tissue exchange in the area of tooth movement to enhance the removal of bone breakdown products, and to enhance the supply of elements necessary for the formation of new bone; and little or no areas of hyalinization or necrosis of tissue, so that root resorption by cementum necrosis does not occur.

The pulsation or vibrational nature of the force applied to the tooth by the appliance of the invention also helps to break down tissue resistance, as mentioned above. The fibrous elements of the adjacent tissue tend to give way more easily to the moving tooth mass, as the tooth is vibrated, and the tooth moves along the path of least resistance. The vibrating tooth mass more easily separates the fibrous elements and moves more easily through the adjacent bone. The increased circulation and vibrational effect occurs not only in the local area, but flows to adjacent tissues to aid in their adjustment, as teeth are moved through bone, and the total bony architecture is changed.

As a result, the use of the pulsating orthodontic appliance of the present invention results in faster movement of the tooth; reduction of root resorption during orthodontic movement; reduction of horizontal bone loss during bone reconstruction; reduced discomfort from heavy orthodontic pressures; and reduction in tooth extrusion from their boney sockets when pressurized.

The total effect resulting from the use of the orthodontic appliance of the invention is that tooth movement is of a physiological nature causing little or no irreversible results to the tooth or horizontal bone level, and expediting the travel of the tooth along its path through the adjacent bone so as to obtain the most rapid orthodontic movement in a painless environment.

Most orthodontic problems of dental protrusion and/or tooth size arch length discrepancies can be corrected by the use of the pulsating appliance of the present invention. Moreover, the conventional therapy of bicuspid extraction is eliminated when the appliance of the invention is used and, instead, third molars may be extracted and all posterior teeth moved distally.

DETAILED DESCRIPTION OF THE ILLUSTRATED EMBODIMENTS

Figure 1:
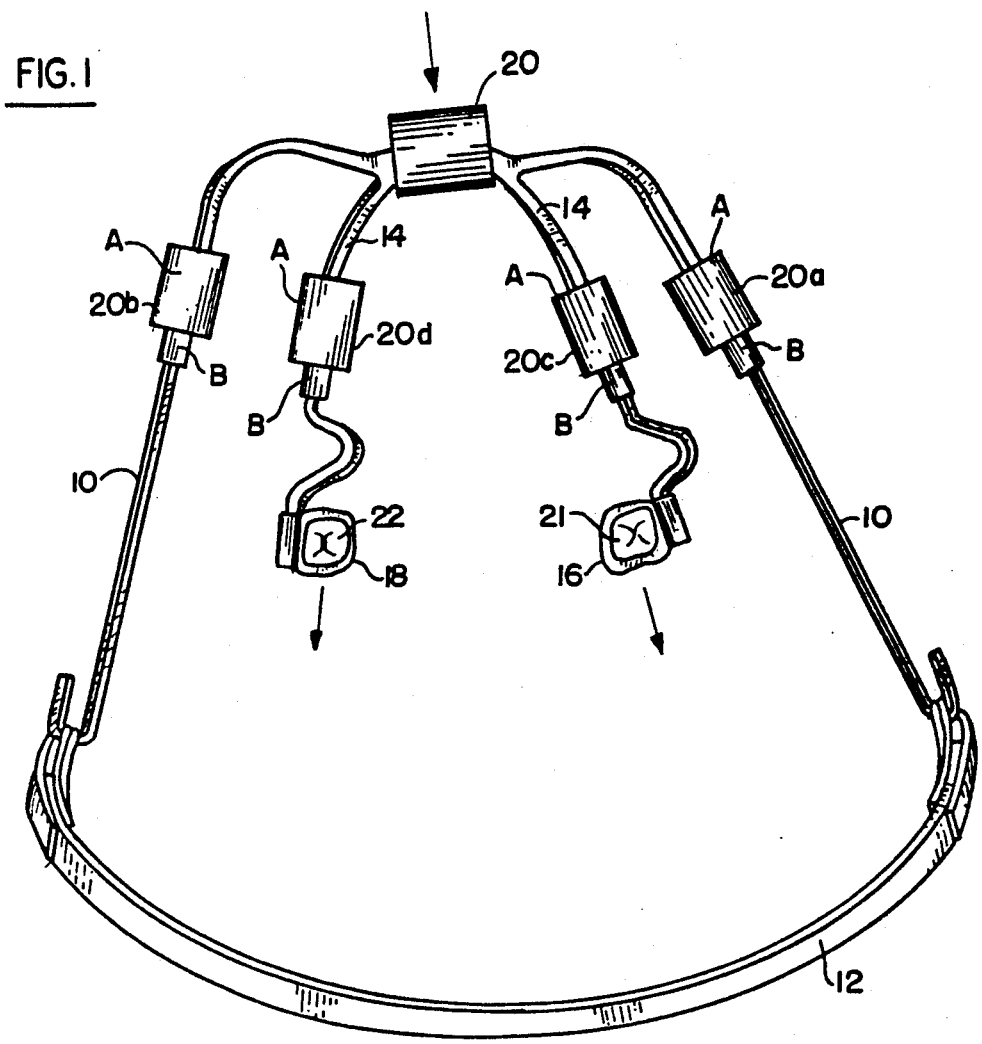
FIG. 1 shows one embodiment of the invention as applied to a posterior cervical extra oral appliance.
Figure 2:
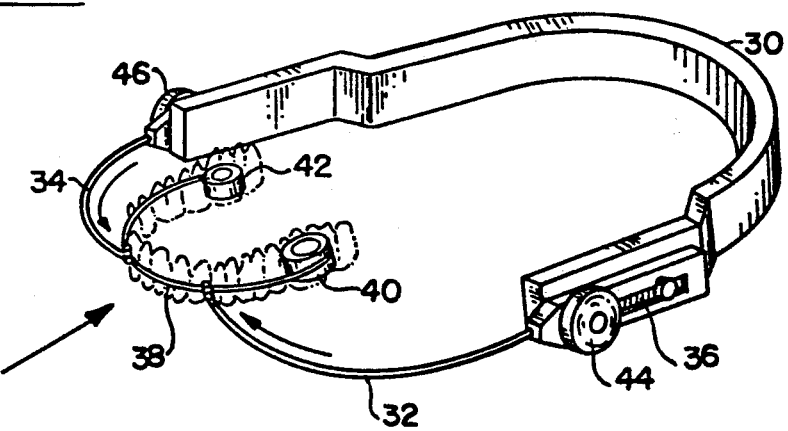
FIG. 2 shows the invention as applied to an anterior cervical extra oral appliance.
Figure 3:
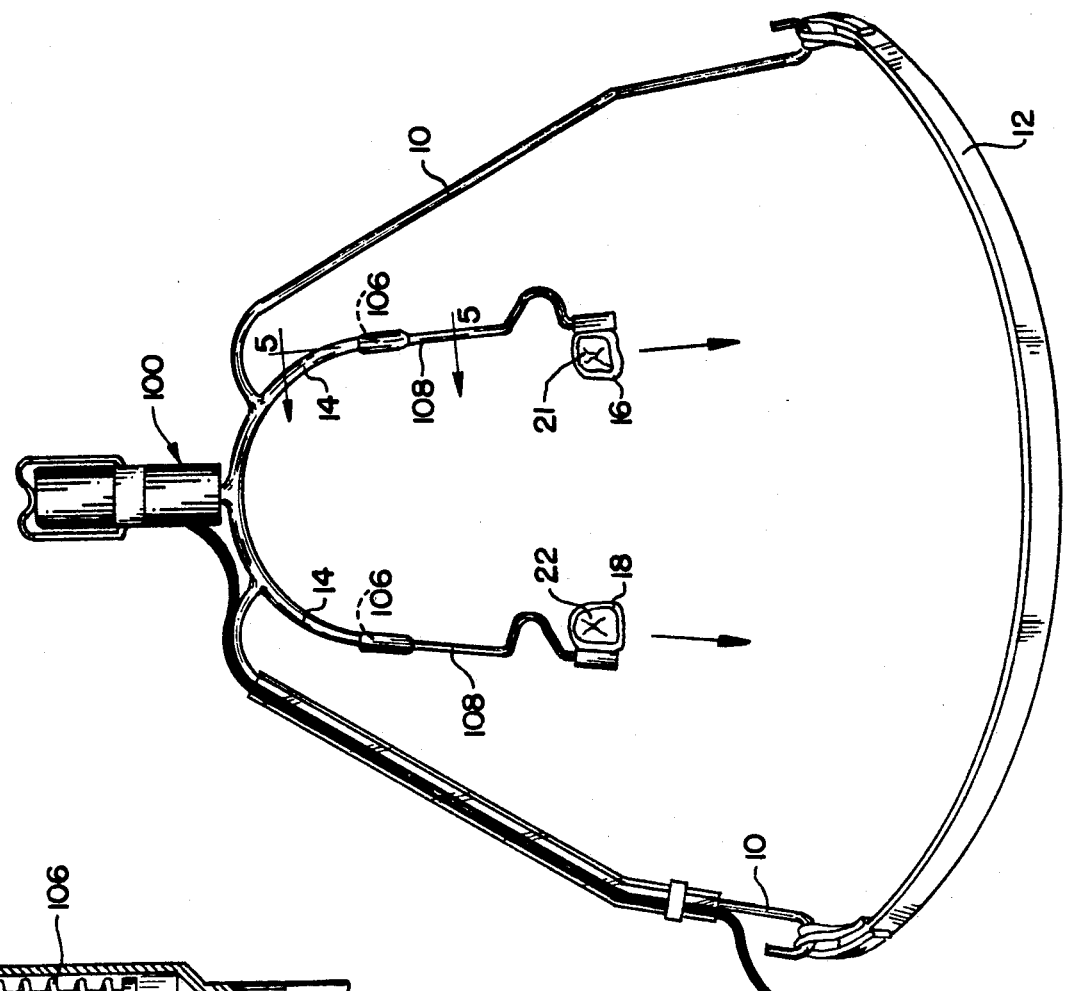
FIG. 3 is a representation of a further embodiment of the invention, similar to the embodiment of FIG. 1.

In the embodiments illustrated in FIGS. 1, 2 and 3, the concept of the present invention is incorporated into various types of cervical extra oral appliances. In these embodiments, a vibrating or pulsating unit is attached to, or is part of, the regular cervical extra oral headgear appliance. The pulsating unit delivers pulsations to the upper or lower posterior teeth through attachments which connect the teeth to the extra oral appliance. In these embodiments, the pulsating unit, is preferably electrical, and it is energized by its own battery-operated motor to activate the extra oral appliance while it is being worn. The motor battery is preferably rechargeable, so that it may be recharged from a conventional 120-volt receptacle, through an appropriate recharging unit, when the appliance is not being worn. Miniature battery-operated pulsating electric motors are available on the market which are suitable for the purpose. The resulting pulsating cervical extra oral appliances, incorporating the concepts of the invention, may be used to direct a pulsation pressure to the molars in a distal direction. The pulsation pressure may be used to move the maxillary or mandibular molars individually, or both simultaneously.

Once the posterior teeth have been moved distally by the appliance, then the anterior teeth may be moved distally by elastic or spring pressure that uses the distally moved molars as anchorage. It may be necessary to extract the third molars to make room for the first and second molars as they move distally.

The present invention makes it possible to correct maxillary or mandibular dental protrusion and/or tooth size arch length discrepancies without bicuspid extraction. Instead of removing teeth in the arch, such as the bicuspids, which has been customary in the prior art orthodontic treatment, only third molar extractions are required when the appliance of the present invention is used, followed by the pulsational movement of the first and second molars distally to correct orthodontic dental protrusions and/or arch length deficiency problems.

The appliance shown in FIG. 1 is a posterior cervical extra oral headgear appliance which includes the usual external oral arch bow 10 which is hooked to an elastic retaining band 12. The band 12 extends around the back of the head or neck of the wearer. The appliance of FIG. 1 also includes an intra oral internal arch bow 14. The ends of bow 14 are coupled to usual tooth bands 16 and 18 which are mounted on molars 21 and 22 which are to be moved distally.

In accordance with the present invention in the embodiment of FIG. 1, a battery-operated electric pulsating motor 20 is mounted, for example, at the junction of the external and internal bows, so that a pulsating pressure may be exerted on the molars 21 and 22 through the arch bow 14. As an alternative, a pair of pulsating motors 20a and 20b may be mounted, as shown on the external arch bow, or a pair of pulsating motors 20c and 20d may be mounted on the internal arch bow 14. The pulsating motors 20a, 20b, 20c and 20d may each include a housing "A" and a reciprocating shaft "B". The motors are interposed in the bows 10 and 14 with one end of the housing being secured to the corresponding bow, and the shaft B also being secured to the corresponding bow, so that the motor and its shaft is interposed between two separate ends of the corresponding bow. Then, when each motor is energized, the shaft B is caused to move reciprocally in and out with respect to the housing A, so as to set up the desired pulsating action.

As described above, when the posterior cervical extra oral appliance of FIG. 1 is used, a pulsating force is applied to the molars 21 and 22 to move the molars in a distal direction, as indicated by the arrows.

FIG. 2 is a representation of an anterior cervical extra oral appliance which, likewise, incorporates the concept of the present invention. The appliance of FIG. 2 includes a rigid retaining band 30 and a mouth brace including a pair of intraoral hooks 32 and 34. The hooks are coupled to the band 30 through spring units, such as the spring unit 36, so that a desired force may be inserted by the hooks on an arch wire 38, the arch wire being secured to selected molars by usual tooth bands 40 and 42. A pair of battery-operated electric pulsing units 44 and 46 are coupled to the intraoral hooks 32 and 34.

As shown, the appliance of FIG. 2 is attached to the anterior teeth, and the pulsation pressure delivered by way of the intraoral hooks 32 and 34 to the anterior maxillary or mandibular teeth serves to produce distal movement of the teeth.

The battery-operated electrical pulsating units referred to above may be of the type used, for example, in electric toothbrushes, such as fully described in U.S. Pat. Nos. 3,156,804; 3,142,852; and 3,187,360. As fully described in the patents, battery-operated electrical pulsating units are well known to the art. Such units comprise a housing and a shaft extending out from the housing, the shaft moving reciprocally in and out when the unit is energized. In the embodiment of FIG. 1, for example, the pulsating motor 20 may be mounted on the external bow, and its pulsating shaft may be attached to the internal bow, so as to achieve the desired pulsating action. The pulsating motors 20a—20d, on the other hand, may be interposed in the extra oral and internal bows, so that their housings are attached at one end, and their shafts are attached at the other end, so as to achieve the desired pulsating action.

The embodiment of FIG. 3 is similar to the embodiment of FIG. 1, and like elements have been designated by the same numbers.

In the embodiment of FIG. 3, a pulsating solenoid 100 is mounted at the junction of the internal bow 14 and external bow 10 of the headgear. The solenoid 100 is a low-voltage solenoid and it is powered by a low-voltage power supply 101. Power supply 101 is energized from the usual alternating current mains. The power supply includes an ON-OFF switch 102, and a lamp 104 which indicates when the solenoid 100 is energized. When the solenoid 100 is energized its plunger 100a is moved rapidly inwardly to strike against the lower end of housing 100b, and the plunger is then returned to its upper position by a spring 100c. This action of the plunger is repeated at a relatively high rate which sets up desired vibrations in the headgear.

Figure 5:
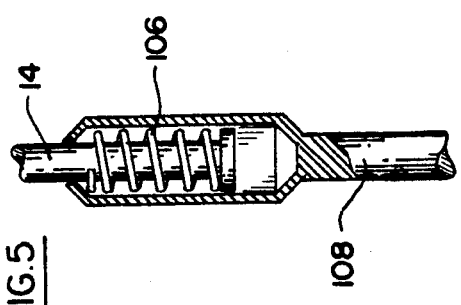
FIG. 5 is a section taken along the lines 5—5 of FIG. 3.
Figure 4:
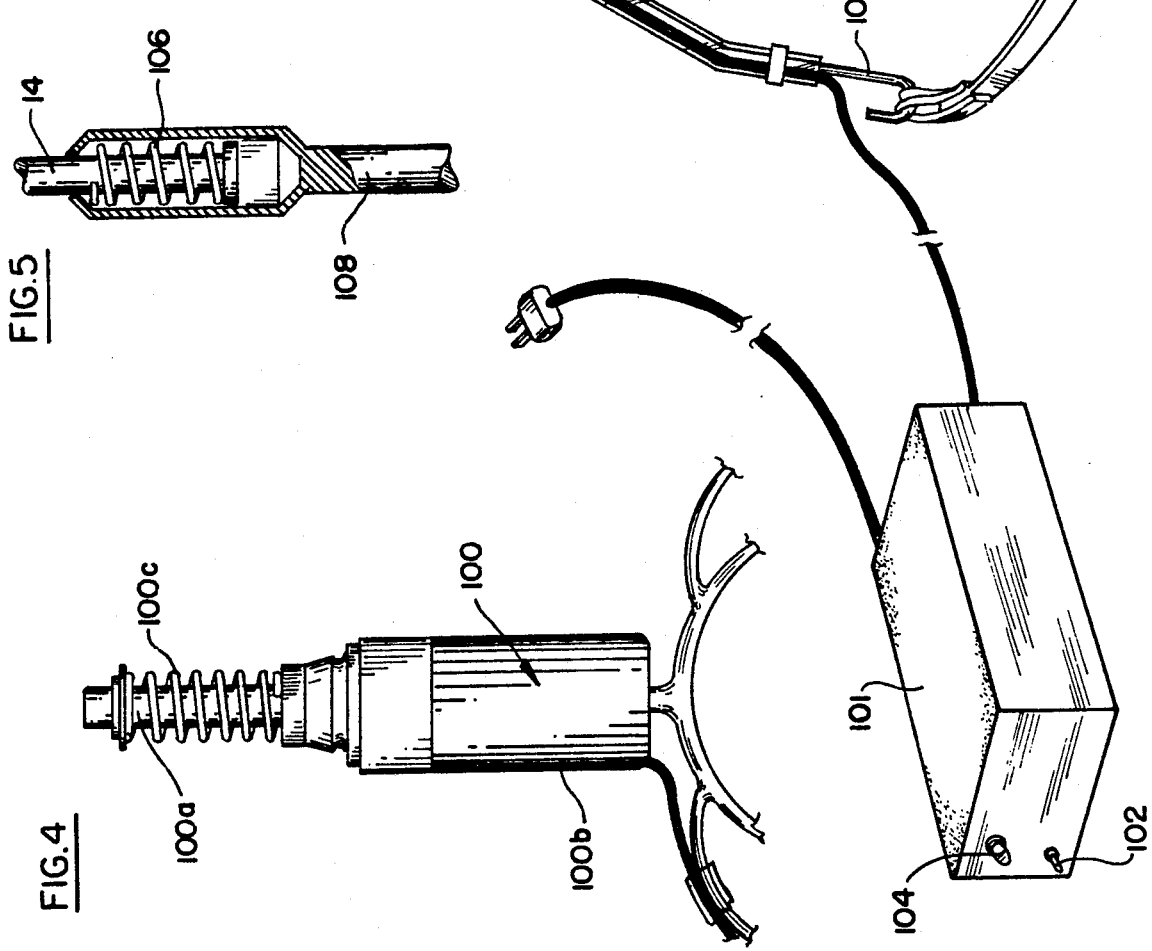
FIG. 4 is a view of a solenoid used in the embodiment of FIG. 3, with the cover removed.

Spring-loaded piston-cylinder mechanisms 106 (FIGS. 3 and 5) are included in the external bow 10 to provide resiliency to the headgear during the vibrations so that the vibrational force on the teeth 16 and 18 will not be too abrupt.

It will be appreciated that while particular embodiments of the invention have been shown and described, modifications may be made. It is intended in the claims to cover the modifications which come within the spirit and scope of the invention.

What is claimed is:

1. An orthodontic appliance comprising: a bow element comprising an external oral arch bow and an internal oral arch bow adapted to be engaged with a band on a tooth to apply a force to the tooth to move the tooth in a predetermined direction in the mouth of a patient; and an electric pulsating motor coupled to said bow element to exert a reciprocating force on said bow element to cause said bow element to exert a pulsating force on the tooth.

2. The orthodontic appliance defined in claim 1, in which said external oral arch bow of said bow element comprises the extra oral arch bow of a posterior cervical extra oral appliance.

3. The orthodontic appliance defined in claim 1, in which said internal oral arch bow of said bow element comprises the intraoral hook of an anterior cervical extra oral appliance.

4. The orthodontic appliance defined in claim 1, and which includes resilient means mounted in said internal oral arch bow of said bow element to cause the pulsating force exerted on the tooth to be less rigid.

* * * * *